United States Patent [19]

Kleemann et al.

[11] 4,339,591
[45] Jul. 13, 1982

[54] PROCESS FOR THE PRODUCTION OF CABOXYLIC ACID CYANIDES

[75] Inventors: Axel Kleemann, Hanau; Bernd Lehmann, Freigericht; Herbert Klenk, Hanau, all of Fed. Rep. of Germany

[73] Assignee: Degussa Aktiengesellschaft, Frankfurt, Fed. Rep. of Germany

[21] Appl. No.: 246,313

[22] Filed: Mar. 23, 1981

[30] Foreign Application Priority Data

Mar. 24, 1980 [DE] Fed. Rep. of Germany ....... 3011305
Oct. 14, 1980 [EP] European Pat. Off. ........... 80106231

[51] Int. Cl.$^3$ ................. C07D 333/24; C07D 307/54; C07C 120/04
[52] U.S. Cl. ................................ 549/72; 260/545 R; 549/483
[58] Field of Search ..................... 260/545 R, 347.3; 549/72

[56] References Cited

U.S. PATENT DOCUMENTS 4,108,875  8/1978  Klenk et al. ...................... 260/347.8
4,143,068  3/1979  Findeisen ......................... 260/545 R

FOREIGN PATENT DOCUMENTS 2614242 10/1977 Fed. Rep. of Germany .
2708182 12/1978 Fed. Rep. of Germany .

Primary Examiner—Dolph H. Torrence
Attorney, Agent, or Firm—Cushman, Darby & Cushman

[57] ABSTRACT

There are produced carboxylic acid cyanides, e.g., acyl cyanides by reacting a carboxylic acid halide with an alkali cyanide or hydrogen cyanide in the presence of a copper (I) salt and a carboxylic acid nitrile. Especially advantageous are glutaric acid dinitrile and 2-methyl glutaric acid dinitrile.

26 Claims, No Drawings

PROCESS FOR THE PRODUCTION OF CABOXYLIC ACID CYANIDES

BACKGROUND OF THE INVENTION

The invention is directed to a process for the production of carboxylic acid cyanides, e.g., acyl cyanides by reaction of a carboxylic acid halide with an alkali metal cyanide or hydrogen cyanide in the presence of a copper (I) salt and a carboxylic acid nitrile.

It is known to produce carboxylic acid cyanides from carboxylic acid halides by reacting the halides in the presence of catalytic amounts of copper (I) cyanide, copper (II) cyanide, zinc cyanide or their complex compounds with alkali cyanides or hydrogen cyanide at a temperature of 100° to 300° C. (German AS No. 2614242 and related Findeisen U.S. Pat. No. 4,143,068, the entire disclosure of the Findeisen U.S. patent being hereby incorporated by reference and relied upon). The disadvantage in this process is that to produce suitable transformations relatively high temperatures, chiefly above 200° C., and/or long reaction times are needed. However, side reactions are favored under these conditions, especially the formation of dimers so that the yields are moderate. With certain carboxylic acid cyanides, for example, with the lower aliphatic carboxylic acid cyanides, the yields only amount to a few percent.

It is also known to carry out the reaction of the carboxylic acid halide with an alkali metal cyanide in the presence of a copper (I) salt and a carboxylic acid nitrile, especially acetonitrile and thereby to operate at a temperature from 50° to 180° C. (German OS No. 2708182 and related Klenk U.S. Pat. No. 4,108,875, the entire disclosure of which is hereby incorporated by reference and relied upon). It is true that in this process relatively low temperatures are sufficient; however, the reaction times are undesirably long and the yields of carboxylic acid cyanide are not satisfactory.

SUMMARY OF THE INVENTION

There has now been found a process for the production of carboxylic acid cyanides by reaction of a carboxylic halide with an alkali cyanide or hydrogen cyanide in the presence of a copper (I) salt and a carboxylic acid nitrile characterized by using a carboxylic acid nitrile of the formula

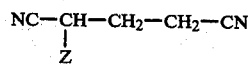

in which Z is a hydrogen atom or a methyl group. Although this process is operated at the same temperatures as the process according to German OS No. 2708182 and Klenk U.S. Pat. No. 4,108,875, there suffice very much shorter reaction times to obtain higher amount of transformation. There are produced considerably better yield of the carboxylic acid cyanide. Even the lower aliphatic carboxylic acid cyanides, such as acetyl cyanide, are producible with excellent yields.

The process of the invention serves with advantage for the production of carboxylic acid cyanides of the formula

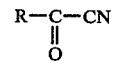

in which R is an unbranched or branched alkyl group with preferably 1 to 7 carbon atoms and especially 1 to 4 carbons, a cycloalkyl group with preferably 3 to 6 carbon atoms and especially 3 carbon atoms in the ring, a cycloalkyl group preferably with 3 to 6 carbon atoms in the ring and having one or more methyl substituents, a phenyl group, a furyl group, or a thienyl group by reacting a carboxylic acid halide of the formula

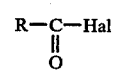

in which R has the previously given meaning, and Hal stands for a bromine or preferably for a chlorine atom.

This type of carboxylic acid halide includes, for example, acetyl bromide, propionyl bromide, butyryl bromide, isobutyryl bromide, valeroyl chloride, valeroyl bromide, isovaleroyl bromide, 2-methylbutyryl bromide, 2,2-dimethylbutyryl bromide, privaloyl bromide, heptanoyl chloride, cyclohexane carboxylic acid chloride, 1-methyl cyclohexane carboxylic acid chloride, cyclopentane carboxylic acid chloride, benzoyl chloride, furan-2-carboxylic acid chloride, thiophene-2-carboxylic acid chloride, 1,3-dimethylcyclopropane carboxylic acid chloride and preferably butyryl chloride, isovaleroyl chloride, 2-methylbutyryl chloride, 2,2-dimethylbutyryl chloride, cyclopropane carboxylic acid chloride and 1-methylcyclopropane carboxylic acid chloride and especially acetyl chloride, propionyl chloride, isobutyryl chloride and pivaloyl chloride.

Of the alkali cyanide, there are preferred sodium cyanide and potassium cyanide. Advantageously, the alkali cyanide is added in the most finely divided form possible, preferably as a suspension in the carboxyic acid nitrile.

There can be used both simple and complex copper (I) salts, particularly for example copper (I) cyanide, copper (I) chloride, copper (I) bromide and potassium tetracyanocuprate (I). There can also be used copper (I) iodide, copper (I) thiocyanate and sodium tetracyanocuprate (I). There can also be used other copper (I) compounds which convert into copper (I) salts under the conditions of reaction, as, for example, copper (I) oxide. In some cases, especially if the reaction is carried out with hydrogen cyanide, it is advantageous to employ copper metal, suitably in powder form. In these cases, copper (II) compounds can be used in place of copper (I) compounds.

The reaction according to the invention takes place in the presence of carboxylic acid nitriles of formula I. These are glutaric acid dinitrile (glutaronitrile) and 2-methylglutaric acid dinitrile. Preferably, there is used 2-methylglutaric acid dinitrile.

In some cases, it is advantageous to employ inert organic solvents as diluents. As solvents, there can be used for example ethers such as dioxane or ethylene glycol diethyl ether or esters such as butyl acetate. Especially suited are aromatic hydrocarbons such as benzene, toluene, and xylenes, or tetralin or aliphatic hydrocarbons such as ligroin having a boiling point of 90° to 140° C. or cyclohexane or halogenated, preferably chlorinated, aromatic, or aliphatic hydrocarbons such as trichloroethylene or especially chlorobenzene, dichlorobenzene, or tetrachloroethane.

What ratios of materials are used namely the carboxylic acid halide, the alkali cyanide, or hydrogen cyanide, the carboxylic acid nitrile and the copper (I) salt and what reaction conditions such as temperature and pressure are chosen depend on the type of materials as well as in a given case on the type and amount of the solvent.

It is generally suitable to use at least about a stoichiometric amount of cyanide—alkali metal cyanide or hydrogen cyanide. Advantageously, there is used about 1.05 to 3.0 equivalents of cyanide, especially 1.05 to 1.5 equivalents of cyanide, per mole of acyl halide, e.g., acyl chloride. It is generally suitable to use about 0.05 to 1.0 equivalent of copper (I) salt per mole of acyl halide. Preferably, there is employed 0.05 to 0.5 equivalent of copper (I) salt per mole of acyl halide. If the copper (I) salt is the cyanide, then there can be saved entirely or partially an equivalent amount of alkali cyanide or hydrogen cyanide. However, it is generally advantageous not to introduce more than about 0.5 equivalent of cyanide in the form of copper (I) salt. Although the copper metal can be used in substantially any amount, it is generally suitable not to employ substantially more than an amount of copper metal equivalent to the copper (I) salt provided for.

Generally, it is suitable to add at least 0.05 mole of nitrile per mole of acyl halide, e.g., acyl chloride. Although the nitrile can be used in a many times molar excess, it is advantageous to use not more than 2 moles of nitrile per mole of acyl halide. Preferably, there are used per mole of acyl halide about 0.1 to 1.5 mole of nitrile, especially 0.1 to 1.0 mole of nitrile.

The reaction is generally carried out at a temperature of about 50° to about 180° C., particularly from 70° to 130° C. Although the pressure can be selected substantially at random, it is advantageous not to deviate substantially from normal pressure, i.e., atmospheric pressure. In some cases, because of the presence of volatile substances, it can be suitable to choose a higher pressure corresponding to the temperature. Besides, it can be advantageous to operate under the exclusion of oxygen.

In the case of the reaction with alkali cyanide, a preferred procedure, which is particularly used with advantage in carrying out the process on an industrial scale (e.g. many kilograms, e.g., 50 kg or more), is to have the carboxylic acid halide present, first heat this to the reaction temperature, and then introduce the alkali cyanide at this temperature. Besides in so doing, it is favorable to have the copper (I) salt present with the carboxylic acid halide and to supply the alkali cyanide as solid material suspended in the carboxylic acid nitrile. In the case of the reaction with hydrogen cyanide, a preferred procedure is to have present a mixture of the carboxylic acid halide with the carboxylic acid nitrile, the copper compound and in a given case the copper metal, to heat this mixture to the reaction temperature and to introduce hydrogen cyanide into the warm mixture.

Unless otherwise indicated, all parts and percentages are by weight.

The process can comprise, consist essentially of, or consist of the stated steps with the materials set forth.

DETAILED DESCRIPTION

EXAMPLE 1

A mixture of 628 grams (8.0 moles) of acetyl chloride, 510 grams (10.4 grams) of sodium cyanide, 72 grams (0.8 mole) of copper (I) cyanide, and 800 grams (7.4 moles) of 2-methylglutaric acid dinitrile were held for 4 hours under reflux at the boiling temperature. Then it was cooled and filtered under suction. The residue was washed with 500 ml of 2-methylglutaric acid dinitrile. The filtrate was distilled. The acetyl cyanide which was thus obtained was 99% as was established by gas chromatography and silverometric cyanide titration. The boiling point of the acetyl cyanide was 93° C. The yield was 375 grams, corresponding to 67%, based on the acetyl chloride employed.

EXAMPLE 2

A mixture of 92.5 grams (1.0 mole) of propionyl chloride, 68.6 grams (1.4 moles) of sodium cyanide, 9.0 grams (0.1 mole) of copper (I) cyanide, and 76 grams (0.7 mole) of 2-methylglutaric acid dinitrile were held for 1 hour under reflux at the boiling temperature. Then it was cooled off and filtered under suction. The residue was washed with 76 grams of 2-methylglutaric acid dinitrile. The filtrate was distilled under reduced pressure. In so doing, there was obtained 66 grams of a 97% propionyl cyanide. This corresponds to a yield of propionyl cyanide of 77% based on the propionyl chloride employed.

EXAMPLE 3

A mixture of 106.5 grams (1.0 mole) of butyryl chloride, 68.6 grams (1.4 moles) of sodium cyanide, 9.0 grams (0.1 mole) of copper (I) cyanide, 14 grams (0.13 mole) of 2-methylglutaric acid dinitrile and 29 grams of tetralin were held for 2 hours under reflux at the boiling temperature. The reaction mixture was then distilled under reduced pressure. Hereby, there were obtained 79 grams of a 97% butryl cyanide. This corresponds to a yield of butryl cyanide of 79% based on the butyryl chloride employed.

EXAMPLE 4

241.2 grams (2.0 moles) of pivaloyl chloride were heated to the boiling temperature with 17.9 grams (0.2 mole) of copper (I) cyanide. In the course of one hour at this temperature under stirring there was added a suspension of 105.9 grams (2.2 moles) of sodium cyanide in 142.5 grams (1.3 moles) of 2-methylglutaric acid dinitrile. The mixture was held for 36 minutes at a temperature up to 130° C. Then it was cooled off and filtered. The residue was washed with 120 ml of 2-methylglutaric acid dinitrile. In the distillation of the filtrate there were obtained 209 grams of 98% pivaloyl cyanide. This corresponds to a yield of pivaloyl cyanide of 94% based on the pivaloyl chloride employed.

EXAMPLE 5

The procedure was according to Example 4 but instead of pivaloyl chloride there were employed 213.1 grams (2.0 moles) of isobutyryl chloride. In the distillation there were obtained 155 grams of pure isobutyryl cyanide, corresponding to a yield of 80% based on the isobutyryl chloride employed.

EXAMPLE 6

The procedure was according to Example 2 but instead of propionyl chloride there were employed 120.5 grams (1.0 mole) of 2-methylbutyryl chloride and the mixture was held for 1.5 hours at a temperature up to 130° C. In the distillation there were obtained 98 grams of pure 2-methylbutryl cyanide, corresponding to a yield of 88%, based on the 2-methylbutyryl chloride employed.

EXAMPLE 7

The procedure was according to Example 2 but there were added 120.5 grams (1.0 mole) of 3-methylbutyryl chloride and the mixture was held for 1.5 hours at a temperature up to 130° C. In the distillation there were obtained 100 grams of a 96% 3-methylbutyryl cyanide. This corresponds to a yield of 3-methylbutyryl cyanide of 86% based on the 3-methylbutyryl chloride employed.

EXAMPLE 8

The procedure was according to Example 2 but instead of methylglutaric acid dinitrile there were employed 76 grams (0.8 mole) of glutaric acid dinitrile and the mixture was held for 1.5 hours under reflux at the boiling temperature. In the distillation there were obtained 64 grams of a 97% propionyl cyanide. This corresponds to a yield of propionyl cyanide of 75% based on the propionyl chloride employed.

EXAMPLE 9

A mixture of 104.5 grams (1.0 mole) of cyclopropane carboxylic acid chloride, 68.6 grams (1.4 mole) of sodium cyanide, 9.0 grams (0.1 mole) of copper (I) cyanide and 67 grams of 2-methylglutaric acid dinitrile were held for 1 hour with stirring at a temperature of 120° to 130° C. Then it was cooled off and filtered. The residue was washed with 67 grams of 2-methylglutaric acid dinitrile. The filtrate was distilled under reduced pressure. Hereby there were obtained 78 grams of 99% cyclopropane carboxylic acid cyanide, corresponding to a yield of 81% based on the cyclopropane carboxylic acid chloride employed. The boiling point of the cyclopropane carboxylic acid cyanide was 78° C. at 88 mbar.

EXAMPLE 10

The procedure was according to Example 9 but instead of cyclopropane acid chloride there were employed 140.5 grams (1.0 mole) of benzoyl chloride. In the distillation there were obtained 122 grams of 97% benzoyl cyanide, corresponding to a yield of 91% based on the benzoyl chloride employed. The boiling point of the benzoyl chloride was 93° C. at 16 mbar.

EXAMPLE 11

A mixture of 120.6 grams (1.0 mole) of pivaloyl chloride, 9.0 grams (0.1 mole) of copper (I) cyanide, 6.4 grams (0.1 gram atom) of pulverized copper and 150 ml of 2-methylglutaric acid dinitrile were treated in the course of 6 hours with 29.7 grams (1.1 moles) of hydrogen cyanide. The mixture in the meanwhile was held under nitrogen at a temperature of 90° to 110° C. Hereby there escaped hydrogen chloride and hydrogen cyanide; the hydrogen cyanide was condensed and returned. From the reaction mixture by fractional distillation under reduced pressure there were obtained 10 grams of pivaloyl chloride and 96 grams of 98% pivaloyl cyanide. The yield of pivaloyl cyanide amounted to 85% based on the pivaloyl cyanide employed. For further batches in each case there was used the residue remaining in the distillation of the previous reaction mixture. To these there were added first 120.6 grams (1.0 mole) of pivaloyl chloride and then in the course of 6 hours 29.7 grams (1.1 moles) of hydrogen cyanide. For the rest the process was as previously described. The yields of pivaloyl cyanide amounted to 86 to 88% based on the pivaloyl chloride employed.

EXAMPLE 12

There were simultaneously fed into 110 grams of 2-methylglutaric acid dinitrile 29.7 grams (1.1 moles of hydrogen cyanide and 198 grams of a 30% solution of sodium methylate in methanol (corresponding to 1.1 moles of sodium methylate). The methanol was expelled from the mixture under reduced pressure. The thus produced sodium cyanide suspension within a period of 5 minutes was introduced into a mixture of 120.6 grams (1.0 mole) of pivaloyl chloride and 9.0 grams (0.1 mole) of copper (I) cyanide. The temperature of the mixture was held hereby and for a further 10 minutes at 125° to 130° C. There were obtained 107 grams of 98% pivaloyl cyanide, corresponding to a yield of 95% based on the pivaloyl chloride employed.

The entire disclosure of German priority application No. P 3011305.4 and European Patent Office application No. 80106231.6 are hereby incorporated by reference.

What is claimed is:

1. In a process for the production of a carboxylic acid cyanide by reaction of a carboxylic acid halide with an alkali cyanide or hydrogen cyanide in the presence of copper (I) salt and a carboxylic acid nitrile, the improvement comprising employing as the carboxylic acid nitrile a dinitrile of the formula

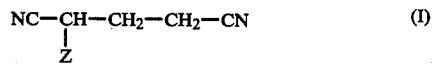

where Z is a hydrogen atom or the methyl group.

2. The process of claim 1 wherein there is employed 0.1 to 1.5 moles of the dinitrile per mole of carboxylic acid halide.

3. The process of claim 1 wherein there is employed an alkali cyanide.

4. The process of claim 1 wherein there is employed hydrogen cyanide.

5. The process of claim 1 wherein there is produced an acyl cyanide of the formula

where R is alkyl of 1 to 7 carbon atoms, a cycloalkyl group having 3 to 6 carbon atoms in the ring, a cycloalkyl group having 3 to 6 carbon atoms in the ring and at least one methyl group on the ring, a phenyl group, a furyl group or a thienyl group and the carboxylic acid halide is an acyl halide of the formula

where Hal is chloride or bromine.

6. The process of claim 5 which is carried out at 50° to 180° C. and there are employed 1.05 to 3.0 equivalents of cyanide per mole of acyl halide, 0.05 to 1.0 equivalents of copper (I) salt per mole of acyl halide and at least 0.05 mole of dinitrile per mole of acyl halide.

7. The process of claim 6 wherein the copper (I) salt is copper (I) cyanide.

8. The process of claim 6 wherein the copper (I) salt is copper (I) cyanide, copper (I) chloride, copper (I) bromide or potassium tetracyanocuprate (I).

9. The process of claim 6 wherein R is furyl or thienyl.

10. The process of claim 6 wherein R is alkyl of 1 to 7 carbon atoms, cycloalkyl of 3 to 6 carbon atoms or methyl cycloalkyl of 3 to 6 carbon atoms.

11. The process of claim 10 wherein R is alkyl of 1 to 7 carbon atoms.

12. The process of claim 11 wherein R is alkyl of 1 to 4 carbon atoms.

13. The process of claim 10 where R is cycloalkyl 3 to 6 carbon atoms or methyl cycloalkyl of 3 to 6 carbon atoms.

14. The process of claim 13 where R is cyclopropyl or mono or dimethyl cyclopropyl.

15. The process of claim 14 where R is cyclopropyl.

16. The process of claim 6 where R is phenyl.

17. The process of claim 6 where there is also present an inert organic solvent.

18. The process of claim 17 wherein the inert organic solvent is a hydrocarbon, halohydrocarbon, ether or ester.

19. The process of claim 18 wherein the inert organic solvent is a hydrocarbon or halohydrocarbon.

20. The process of claim 19 wherein the inert solvent is an aromatic hydrocarbon or a cycloaliphatic hydrocarbon.

21. The process of claim 6 wherein there are used 0.05 to 0.5 equivalents of copper (I) salt per mole of acyl halide and Hal is chlorine.

22. The process of claim 21 wherein there are used 0.05 to 2 moles of dinitrile per mole of acyl halide.

23. Th process of claim 6 wherein the cyanide is sodium cyanide or potassium cyanide and there is used 1.05 to 1.5 equivalents of cyanide per mole of acyl halide.

24. The process of claim 6 wherein the cyanide is hydrogen cyanide and there is used 1.05 to 1.5 equivalents of cyanide per mole of acyl halide.

25. The process of claim 22 wherein there is employed 0.1 to 1.0 mole of dinitrile per mole of acyl cyanide.

26. The process of claim 6 wherein Z is methyl.

* * * * *